United States Patent [19]

Maeda et al.

[11] Patent Number: 5,001,118

[45] Date of Patent: Mar. 19, 1991

[54] METHOD FOR PREVENTING SENESCENCE AND INCREASING BONE MASS

[75] Inventors: Yuji Maeda, Nagareyama; Hideyuki Yamato, Tokyo; Toru Hirai, Kawagoe; Masanori Ikuzawa, Tachikawa; Mikio Matsuki, Hiratsuka; Masanori Togawa, Kodaira; Eiji Inoguchi, Tokyo; Sinji Nakajima, Kawaguchi; Tadaaki Kato, Tokyo; Chikao Yoshikumi, Kunitachi, all of Japan

[73] Assignee: Kureha Kagaku Kogyo Kabushiki Kaisha, Tokyo, Japan

[21] Appl. No.: 131,399

[22] Filed: Dec. 10, 1987

[30] Foreign Application Priority Data

Dec. 29, 1986 [JP] Japan .................. 61-309392
Dec. 29, 1986 [JP] Japan .................. 61-309393

[51] Int. Cl.$^5$ .............................. A61K 31/59
[52] U.S. Cl. .................................... 514/167
[58] Field of Search ......................... 514/167

[56] References Cited

U.S. PATENT DOCUMENTS

| | | | |
|---|---|---|---|
| 3,715,374 | 2/1973 | DeLuca | 260/397.2 |
| 3,994,878 | 11/1976 | Partridge, Jr. et al. | 260/397.2 |
| 4,230,701 | 10/1980 | Holick et al. | 514/167 |
| 4,292,249 | 9/1981 | Nishikawa et al. | 260/397.2 |
| 4,338,250 | 7/1982 | DeLuca et al. | 260/397.2 |
| 4,442,093 | 4/1984 | Maeda et al. | |
| 4,456,553 | 6/1984 | Oshida et al. | 260/397.2 |
| 4,501,737 | 2/1985 | Yamato et al. | |
| 4,501,738 | 2/1985 | Yamato et al. | |
| 4,534,975 | 8/1985 | Yamato et al. | |
| 4,590,184 | 5/1986 | Maeda et al. | |
| 4,628,050 | 12/1986 | Maeda et al. | |

OTHER PUBLICATIONS

*Nutr. Metabol.*, vol. 18, pp. 99–104 (1975).
*Aviation, Space, and Environmental Medicine*, vol. 54, pp. 447–451 (1983).
*Calcified Tissue Int.*, vol. 39, No. 3, 1986, pp. 128–132, B. J. Rus et al., "Does 24R,25(OH) 2-Vitamin D3 Prevent Postmenopausal Bone Loss?".
*Vitamin D; A Chemical, Biochemical and Clinical Update*, 1985, pp. 1041–1042, T. S. Lindholm et al., "Treatment of Calcium Deficiency Osteoporosis...".
*British Medical Journal*, vol. 2, No. 6146, Oct. 28, 1978, pp. 1196–1197, Y. Weisman et al., "Serum 24,25-Dihroxyvitamin D Concentration in Femoral...".
*Acta Endocrinologica*, vol. 101, 1982, pp. 636–640, J. Reeve et al., "Long-term Treatment of Osteoporosis w/ 24,25 Dihydroxycholecalciferol."
*Adv. Exp. Med. Biol.*, vol. 103, 1977 (Published 1978), pp. 487–503, R. G. G. Russell et al., "Physiological and Pharmacological Aspects of 24,25...".
*Kosm. Biol. Avia Kosm. Med.*, vol. 16, No. 5, 1982, pp. 74–77, I. N. Sergeev et al. "The Role of 24,25-Dihydroxychloecalciferol in Bone Mineralization of...".
*Revue Du Rhumatisme*, vol. 46, No. 10, 1979, pp. 517–519, A. Prier et al., "Dosage Rediocompetitif de la 25-hydroxyvitamine D et de la 24,25-...".
*J. Clin. Invest.*, vol. 73, No. 6, Jun. 1984, pp. 1668–1672, K-S. Tsai et al., "Impaired Vitamin D Metabolism w/ aging in women".
*J. Nutr.*, vol. 107, 1977, pp. 194–198, A. Boris et al., "Relative Activities of Some Metabolites and Analogs of Cholecalciferol in Stimulation of...".

Primary Examiner—H. M. S. Sneed
Assistant Examiner—J. Saba
Attorney, Agent, or Firm—Oblon, Spivak, McClelland, Maier & Neustadt

[57] ABSTRACT

Disclosed herein is a method for preventing senescence and increasing bone mass namely, bone volume and bone strength which method comprises administering 24,25-dihydroxy cholecalciferol in a pharmaceutically effective amount, and also use of 24,25-dihydroxy cholecalciferol for preparing anti-senescent compositions and compositions for increasing bone mass.

2 Claims, 2 Drawing Sheets

FIG. 2 (a)

Test with a 20-kg load cell
Plunger speed 50 mm/min
Chart speed 720 mm/min

Load (kg)

Control group

Amount of displacement

FIG. 2 (b)

Load (kg)

Group of administration of the present substance

Amount of displacement

METHOD FOR PREVENTING SENESCENCE AND INCREASING BONE MASS

BACKGROUND OF THE INVENTION

The present invention relates to a method for preventing senescence, particularly bone senescence, which method comprises administering 24,25-dihydroxy cholecalciferol in a pharmaceutically effective amount.

The present invention relates further to a method for increasing bone mass, namely a method for increasing bone volume and increasing bone strength, which method comprises administering 24,25-dihydroxy cholecalciferol in a pharmaceutically effective amount.

In Japan, population of the aged 65 years or over old is steadily increasing at a rate far greater than that in any other foreign country. It has been demonstrated that the bone volume in the aged tends physiologically to decrease as they grow old. It is generally held that the bone volume of a person begins to decrease about when the person becomes forty. Thus, the decrease of bone volume serves as an index of senescence. The bones have a biological significance that they not only play a part of a mechanical support for the whole body but also serve as an important storehouse of calcium ions indispensable to homeostasis of the body. The decrease of bone volume due to senescence, therefore, constitutes itself a serious problem. No medicine safe and capable of preventing sencescence has been available to date.

Owing to the arrival of the so-called senile society in recent years, even when normal persons who do not specifically suffer from disorders in bone metabolism are aged, the aged tend to suffer from the aforementioned decrease of bone volume coupled with the physiological decrease of bone strength and, consequently, tend to suffer a fracture more readily under a feeble external force than in their younger days. In the aged, immobilized osteopenia advances quickly once they suffer a fracture. The increment of bone strength in the aged, therefore, is a very important task. In such circumstances, the development of a medicine safe and capable of increasing bone strength has been urgently expected.

The present inventors have continued a study as to a physiological activity of a substance inherently occurring in the body of a healthy person and exhibiting proven safety and as a result, found that 24,25-dihydroxy cholecalciferol (hereinafter referred to as "the present substance" or as "24,25-$(OH)_2$-$D_3$") possesses numerous physiologically activity. As concerns the bones, they have found that the present substance has an activity of preventing osteoporosis, i.e. one of the disorders in bone metabolism. As the result of their latest experiment on lifelong administration of the present substance to rats, they have found that the present substance has an activity of increasing bone volume (decrease of which is an index of senescence), without affecting the bone quality and thereby preventing senescence. One aspect of the present invention has been perfected based on the above findings. In an extension of the experiment, they have further found that a normal mammal to which the present substance is administered exhibits bone strength clearly surpassing the average bone strength of non-administered normal mammals, and as a result, another aspect of the present invention has been perfected. These findings are literally epochal in the light of the fact that the conventional pharmaceutical compositions for adjusting bone metabolism is found to be only capable of restoring bones having abnormality due to morbidity near to normality. Further, the method for increasing bone volume and the method for increasing bone strength according to the present invention can be effectively applied not only to aged mammals but also to adult mammals and infantile mammals.

When the present invention is applied to adult mammals and aged mammals, not only the bone mass thereof is increased but also the systemic senescence relative to the increment of bone mass is clearly prevented.

From the viewpoint of anti-senescence activity thereof, therefore, the findings which have culminated in the present invention are epochal in the true sense of the word.

The first object of the present invention is to provide a method for preventing senescence, comprising administering 24,25-dihydroxy cholecalciferol in a pharmaceutically effective amount.

The second object of the present invention is to provide a method for increasing bone volume, comprising administering 24,25-dihydroxy cholecalciferol in a pharmaceutically effective amount.

The third object of the present invention is to provide a method for increasing bone strength of a normal mammal, comprising administering 24,25-dihydroxy cholecalciferol in a pharmaceutically effective amount.

The fourth object of the present invention is to provide use of 24,25-dihydroxy cholecalciferol for preparing anti-senescent compositions.

The fifth object of the present invention is to provide use of 24,25-dihydroxy cholecalciferol for preparing compositions for increasing bone volume.

The sixth object of the present invention is to provide use of 24,25-dihydroxy cholecalciferol for preparing compositions for increasing bone strength of a normal mammal.

SUMMARY OF THE INVENTION

In a first aspect of the present invention, there is provided a method for preventing senescence, comprising administering 24,25-dihydroxy cholecalciferol in a pharmaceutically effective amount.

In a second aspect of the present invention, there is provided a method for increasing bone volume, comprising administering 24,25-dihydroxy cholecalciferol in a pharmaceutically effective amount.

In a third aspect of the present invention, there is provided a method for increasing bone strength of a normal mammal, comprising administering 24,25-dihydroxy cholecalciferol in a pharmaceutically effective amount.

BRIEF DESCRIPTION OF THE DRAWINGS

FIG. 2 illustrates in charts the results of the measurement of power required for fracturing the femurs of subject animals used in two groups, one for administration of the present substance and the other for control as described in Example 4.

DETAILED DESCRIPTION OF THE INVENTION

Figure 1:
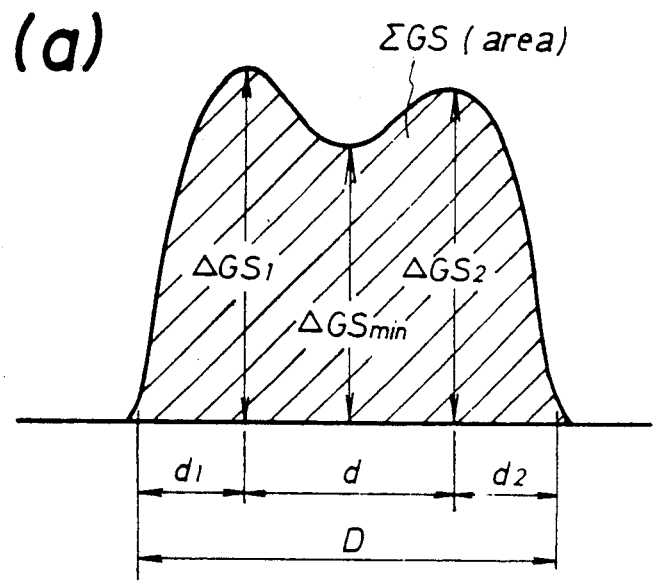
FIG. 1 is a diagram illustrating a bone pattern (represented by Al values) based on the data of the M.D. (microdensitometry) method given in Tables 6 to 8.
Figure 1:
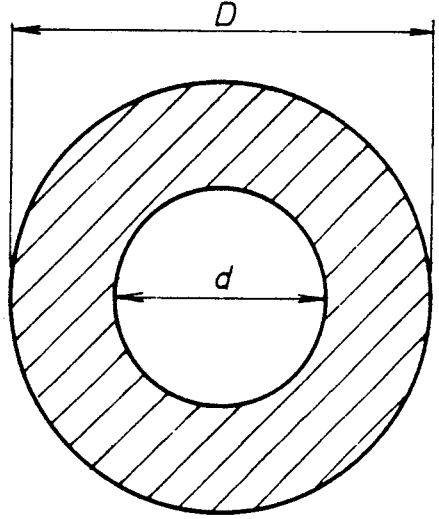

The present invention relates to a method for preventing senescence, a method for increasing bone volume, and a method for increasing bone strength of a normal mammal, which methods comprise each administering 24,25-dihydroxy cholecalciferol in a pharmaceutically effective amount.

Further, the present invention relates to use of 24,25-dihydroxy cholecalciferol for preparing each antisenescent compositions, compositions for increasing bone volume, and compositions for increasing bone strength of a normal mammal.

The term "mammals" as used in the present invention refers to human beings and domestic animals.

The method for preventing senescence and the antisenescent compositions according to the present invention are particularly effective in preventing bone senescence.

The expression "preventing senescence" as used in the present invention means not only preventing the bone senescence by the increment of bone mass but also preventing the consequent systemic senescence.

Further, the method for increasing bone volume and the method for increasing bone strength according to the present invention can be applied as effectively to adult mammals and infantile mammals as well as aged mammals.

The present substance itself which is used for preventing senescence, increasing bone volume, and increasing bone strength and used for preparing pharmaceutical compositions intended for such use according to the present invention is well known in the art, possessed of the following structure, and disclosed in "Pharmacia, 10, 319-322 (1974)", for example.

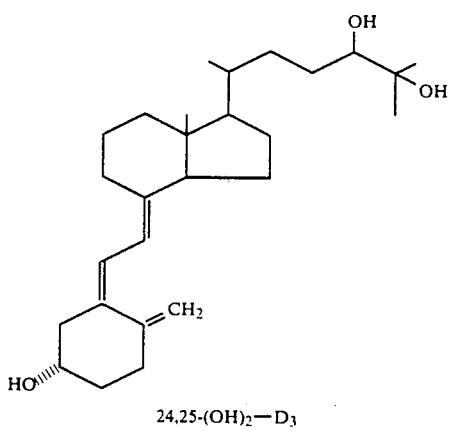

24,25-(OH)$_2$—D$_3$

-continued

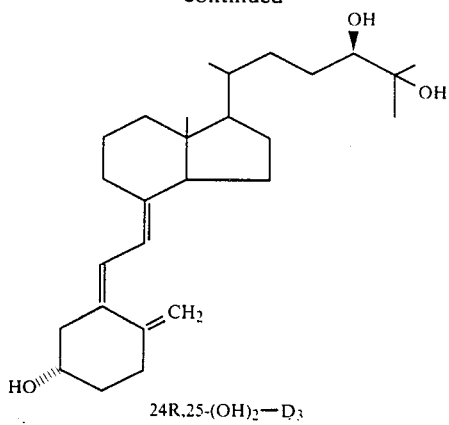

24R,25-(OH)$_2$—D$_3$

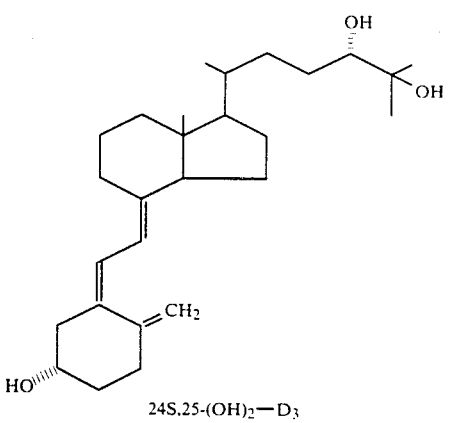

24S,25-(OH)$_2$—D$_3$

The present substance is 24R,25-(OH)$_2$-D3, 24S,25-(OH)$_2$-D3, or possibly a mixture thereof. It is particularly desired to be 24R,25-(OH)$_2$-D3. The compositions for preventing senescence, the compositions for increasing bone volume, and the compositions for increasing bone strength according to the present invention are used in the following various pharmaceutical forms which contain the present substance described above as an active component. The compositions for preventing senescence, the compositions for increasing bone volume, and the compositions for increasing bone strength according to the present invention can be administered orally or parenterally, i.e. by the intraperitoneal, intravenous, subcutanous or intramusclar injection, for example.

The pharmaceutical composition including the present substance as an active component can be used in the administrating form of tablets, powder, granules, capsules, alcohol solution, oily solution, aqueous suspension, etc. Examples of the solvent used for the oily solution include triglyceride esters of a fatty acid of about 8 to about 10 carbon atoms, corn oil, cottenseed oil, peanut oil, cod-liver oil, and oily esters, butter and glycerins are also desirable examples. Examples of other components usable in combination with the present substance include lactose, starch, talc, magnesium stearate, sorbic acid, salts of sorbic acid, sugars and derivatives thereof, alcohols, physiological saline solution, surfactants, and antioxidants.

The unit dose for administration can contain the present substance in a concentration in the range of 0.00002 to 4% by weight, preferably 0.0002 to 1% by weight. The dosage of the present substance is in the range of 0.1 to 100,000 μg, preferably 0.5 to 10,000 μg, per day per adult person.

The present substance was tested for acute toxicity as follows.

ACUTE TOXICITY

A test solution was prepared by dissolving the present substance, 24R,25-$(OH)_2$-$D_3$, in ethanol and again dissolving the resultant ethanol solution in triglyceride ester of a fatty acid of 8 to 10 carbon atoms so that the ethanol concentration is 2%. Then, the test solution was orally administered (p.o.) at a dose of 100 mg/kg to a test group of 10 ICR type male mice (each weighing 25±3 g). For two weeks, the mice were kept under observation for sign of toxication. All of the mice survived showing no sign of abnormality. They were then sacrificed and subjected to biochemical blood inspection, anatomical observation, and histopathological inspection. The results were not different at all from those obtained of a control group of mice to which the above triglyceride ester of the fatty acid containing 2% of ethanol without the present substance was administered. Thus, the $LD_{50}$ value of the present substance for oral administration is not less than 100 mg/kg, indicating that the present substance is definitely safe for the intended use.

Now, the present invention will be described more specifically below with reference to examples demonstrating the effect of the invention. The stereochemical structure at the 24th position C atom of the substance, 24R, 25-$(OH)_2$-$D_3$, used in the examples (different from that used in the examples (different from that of its optical isomer) was confirmed on the basis of the information offered by "Tetrahedron Letters, No. 26, pp 2203–2206, 1975".

EXAMPLE 1

In 1 kg of the triglyceride ester of a fatty acid of 8 to 10 carbon atoms freed from the impurity of reactive peroxide by applying the light of a 400-W high-pressure mercury vapor lamp thereto under continuous argon gas bubbling for 72 hours, 5 mg of the present substance, 24R,25-$(OH)_2$-$D_3$, was dissolved. Then, while dissolving thermally the following components for capsule shell for enclosing the aforementioned solution of the present substance therein, by the conventional method using a soft capsule making machine, soft capsules each containing the 24R,25-$(OH)_2$-$D_3$ in a unit weight of 0.5 μg were prepared (refer to Table 1).

TABLE 1

| Example of components of capsule shell | |
|---|---|
| | (parts by weight*) |
| Gelatin | 10 |
| Glycerol | 2 |
| Antiseptic (Ethyl paraben) | 0.05 |
| Titanium white | 0.2 |
| Water | 0.2 |

*Value in the final phamaceutical composition

Similar soft capsules containing the present substance in varied dose of 1 μg, 2 μg, 5 μg, and 10 μg were prepared by following the procedure described above.

EXAMPLE 2

Solutions obtained by dissolving the present substance, 24R,25-$(OH)_2$-$D_3$ in a prescribed concentration in triglyceride of a fatty acid of 8 to 10 carbon atoms containing 1% of ethanol were administered respectively, orally, forcedly and daily to three male-groups and three female-groups of ICR type mice 5 weeks old at dosages of 10, 100, and 1,000 μg/kg.day. The results are compared below with respect to the following items with those obtained of the male- and female-groups using only the solvent without the present substance. The growth curves obtained by measurement of body weight indicate absence of a discernible difference in change of body weight, respectively between the male-groups and between the female-groups (refer to Tables 2 to 5).

TABLE 2

| | | | General inspection of blood | | | |
|---|---|---|---|---|---|---|
| Sex | Group (10 heads each) | Dosage (μm/kg) | Number of red blood cells | Number of white blood cells | Amount of hemoglobin | Hematocrit value |
| ♂ | I | 10 | — | — | —• | • |
| | II | 100 | — | — | —• | • |
| | III | 1000 | — | — | —• | •• |
| ♀ | IV | 10 | — | — | —• | • |
| | V | 100 | —• | —• | —• | • |
| | VI | 1000 | — | —• | —• | • |

↓ : Decrease below control
— : No difference from control
↑ : Increase above control

TABLE 3

| Dosage (μg/kg) | Sex | GOT | GPT | LDH | Ca | I-P | ALP | T-P | A/G | Alb | T-Bil | Glu | T-CHO | BUN |
|---|---|---|---|---|---|---|---|---|---|---|---|---|---|---|
| 10 | ♂ | — | — | — | — | — | — | — | — | — | — | —• | — | —• |
| 100 | | — | — | — | — | — | — | — | — | — | — | —• | —• | — |
| 1000 | | — | — | ↓ | — | — | — | — | — | —• | ↓ | ↓ | • | ↓ |
| 10 | ♀ | — | — | — | — | — | — | — | — | — | — | —• | • | —• |
| 100 | | — | — | — | — | — | — | — | —• | — | — | • | • | —• |
| 1000 | | — | — | — | — | — | — | — | —• | —• | — | —• | —• | — |

↓ : Decrease below control
— : No difference from control
↑ : Increase above control

TABLE 4

| Dosage (μg/kg) | Sex | pH | Sugar | Protein | Occult blood | Ketone body | Uro-bilinogen |
|---|---|---|---|---|---|---|---|
| 10 | ♂ | → | → | → | → | → | → |
| 100 |  | → | → | → | → | → | → |
| 1000 |  | → | → | → | → | → | → |
| 10 | ♀ | → | → | → | → | → | → |
| 100 |  | → | → | → | → | → | → |
| 1000 |  | → | → | → | → | → | → |

↓ : Decrease below control
→ : No difference from control
↑ : Increase above control

TABLE 5

| Dosage (μg/kg) | Sex | Brain | Pituitary gland | Heart | Lung | Liver | Spleen | Kidney | Adrenal gland | Thymus gland | Testis | Ovary | Uterus |
|---|---|---|---|---|---|---|---|---|---|---|---|---|---|
| 10 | ♂ | → | → | → | → | → | → | → | → | → |  |  |  |
| 100 |  | → | → | → | → | → | → | → | → | → |  |  |  |
| 1000 |  | → | → | → | → | → | → | → | → | → |  |  |  |
| 10 | ♀ | → | → | → | → | → | → | → | → | → |  | → | → |
| 100 |  | → | → | → | → | → | → | → | → | → |  | → | → |
| 1000 |  | → | → | → | → | → | → | → | → | → |  | → | → |

↓ : Decrease below control
→ : No difference from control
↑ : Increase above control The following internal organs were fixed with 10% formalin, tinted with haematoxylin eosine dye, and subjected to histopathological inspection. The test detected no discernible abnormality:

Brain, heart, lung, liver, kidney, adrenal gland, spleen, pancreas, thyroid gland, pituitary gland, thymus, mesentery lymphoglandia, testis, ovary, uterus, stomach, small intestines (jejunum, ileum, and duodenum), large intestines (colon and caecum), orb, submaxillary gland, urinary bladder, dorsal skin, muscle, sternum, sternal medulla, femur, and femoral medulla.

EXAMPLE 3

Procedure

Male Wister rats 4 weeks old were preliminarily kept for two weeks. For the subsequent 24 months, the present substance, $24R,25-(OH)_2-D_3$, was orally administered daily at a dosage of 400 μg/kg.day to the pre-bred rats. Then, the aged rats were sacrificed and their femurs and tibias were collected in the form with adhering flesh, and soft X-ray photographs thereof were taken with a camera (produced by Soflon Corp. and marketed under product code of "Model NST-1005"). By the obtained photographs the volumes of the cortical bone and the sponge bone were measured. Further, as to a part of the femurs the central portion in the direction of the major axis of the femurs was inspected with a microdensitometer thereby analyzing the picture of pattern of shade concentration to calculate the index by the conventional M.D. method. As regards the manner of administration, a modified feed was prepared by uniformly dispersing a prescribed amount of the present substance, $24R,25-(OH)_2-D_3$, in glycine and admixing the resultant dispersing mixture with a marketed feed (produced by Nippon Clea Co., Ltd. under product code of "CE-2") in such a ratio as to give a final glycine concentration of 0.5% by weight, and the modified feed was consumed by the rats. To the rats of the control group, the same marketed feed containing 0.5% by weight of glycine was given.

Results

1. In the group of the rats to which $24R,25-(OH)_2-D_3$ was administered, the cortical bone width, the trabecula of the sponge bone at epiphysis, and the lateral diameter, D (mm) were found to increase in the femurs and the tibias as compared with the rats of the control group.

2. The microdensitometric analysis gave the following results (refer to Tables 6 to 8).

TABLE 6

Results of M.D. analysis

|  | D (mm) | d (mm) | MCI | GSmin | GSmax | ΣGS | $\frac{\Sigma GS}{D}$ |
|---|---|---|---|---|---|---|---|
| Control group | 3.89 ± 0.06 | 2.91 ± 0.26 | 0.252 ± 0.054 | 0.98 ± 0.17 | 1.877 ± 0.06 | 4.80 ± 0.41 | 1.24 ± 0.12 |
| Group of administration of $24R,25-(OH)_2-D_3$ at 400 μg/kg | 4.08** ± 0.05 | 2.12** ± 0.05 | 0.480*** ± 0.01 | 1.62*** ± 0.10 | 2.62*** ± 0.10 | 8.07*** ± 0.662 | 1.98*** ± 0.14 |

X ± S.D.
*P < 0.05
**P < 0.01
***P < 0.001

The symbols, D, d, MCI, GSmin, GSmax, ΣGS, and $D^{GS}$, shown in Table 6 were used in the meanings defined in Table 7.

TABLE 7

Index of analysis

D d $MCI = \frac{d_1 + d_2}{D}$

ΔGS min $\Delta GS\ max = \frac{\Delta GS_1 + \Delta GS_2}{2}$

ΣGS/D

Bone pattern

The numerical values of the terms of the foregoing index of analysis can be determined on the basis of the bone pattern shown in FIG. 1 (represented by Al values).

The symbols of the MD index and the units thereof are as shown in Table 8.

TABLE 8

| Symbol of MD index and unit | | |
|---|---|---|
| Index | Printed signal | Unit |
| D | D | mm |
| $d_1$ | $d_1$ | mm |
| $d_2$ | $d_2$ | mm |
| d | d | mm |
| MCI | MCI | — |
| $\Delta$GSmin | Delta GSmin | mmAl |
| $\Delta GS_1$ | Delta $GS_1$ | mmAl |
| $\Delta GS_2$ | Delta $GS_2$ | mmAl |
| $\Delta$GSmax | Delta GSmax | mmAl |
| $\Sigma$GS | Sigma GS | mm$^2$Al |
| $\Sigma$GS/D | Sigma GS/D | mmAl |

EXAMPLE 4

Male Wister rats 4 weeks old were preliminarily kept for 2 weeks. For the subsequent 24 months, the present substance, 24R,25-(OH)$_2$-D$_3$, was orally administered to the pre-bred rats daily at a dosage of 40 µg/kg.day. Then, the aged rats were sacrificed and their femurs were collected and fractured with an instrument (produced by Iio Denki Co., Ltd. and marketed under trade name of "Rheodynacorder RDR-1500(D)") using a 20 kg-load cell, at a distance of 6.5 mm from the trochanter minor under the condition of a fulcrum interval of 13 mm to determine the power required for the fracture.

As regards the manner of administration, a modified feed was prepared by uniformly dispersing a prescribed amount of the present substance, 24R,25-(OH)$_2$-D$_3$, in glycine and admixing the resultant dispersing mixture with a marketed feed (produced by Nippon Clea Co., Ltd. under product code of "CE-2") in such a manner as to give a final glycine concentration of 0.5% by weight and the modified feed was consumed by the rats. The administration dosage was calculated on the basis of the actual amount of the feed consumed by the rats.

The results of fracture test are illustrated in Table 9.

TABLE 9

| Results of fracture test | |
|---|---|
| Group | Power for fracture ($\times 10^6$ dyn) |
| Control group | 11.6 ± 2.2 |
| Group of administration of 24R,25—(OH)$_2$—D$_3$ at 40 µg/kg | Out of scale, so large that could not be measured |

Charts representing typical data are shown in FIG. 2.

What is claimed is:

1. A method for preventing bone senescence, comprising administering 24R 25-dihydroxycholecalciferol to a patient suffering therefrom in a therapeutically effective amount and thereby preventing bone senescence of the patient.

2. A method for increasing bone volume, comprising administering 24R25-dihydroxycholecalciferol in a therapeutically effective amount to a subject and thereby increasing bone volume of the subject.

* * * * *